(12) United States Patent
Paula-Molina et al.

(10) Patent No.: US 9,794,526 B2
(45) Date of Patent: Oct. 17, 2017

(54) NON-DISRUPTIVE MONITOR SYSTEM

(71) Applicant: SONR LLC, Brooklyn, NY (US)

(72) Inventors: Rene Paula-Molina, Brooklyn, NY (US); Klaus Rosburg, Brooklyn, NY (US); Yanir Hirshberg, San Jose, CA (US)

(73) Assignee: SONR LLC, Brooklyn, NY (US)

( * ) Notice: Subject to any disclaimer, the term of this patent is extended or adjusted under 35 U.S.C. 154(b) by 520 days.

(21) Appl. No.: 14/178,274

(22) Filed: Feb. 12, 2014

(65) Prior Publication Data
US 2015/0228175 A1 Aug. 13, 2015

(51) Int. Cl.
*G08B 21/02* (2006.01)
*H04N 7/18* (2006.01)
*G06F 19/00* (2011.01)

(52) U.S. Cl.
CPC ......... *H04N 7/183* (2013.01); *G06F 19/3418* (2013.01); *G08B 21/0208* (2013.01)

(58) Field of Classification Search
CPC .. H04N 7/183; G06F 19/3418; G08B 21/0208
See application file for complete search history.

(56) References Cited

U.S. PATENT DOCUMENTS

| | | | | |
|---|---|---|---|---|
| 4,010,460 A | * | 3/1977 | DeRosa | G08B 3/105 340/7.58 |
| 6,104,334 A | * | 8/2000 | Allport | G06F 1/1626 340/12.28 |
| 6,462,664 B1 | * | 10/2002 | Cuijpers | H03G 1/02 340/573.1 |
| 2002/0060247 A1 | * | 5/2002 | Krishnaswamy | A61B 5/0002 235/472.01 |
| 2002/0107927 A1 | * | 8/2002 | Gallant | G08B 21/0423 709/206 |
| 2003/0060808 A1 | * | 3/2003 | Wilk | A61G 3/001 606/1 |
| 2003/0067391 A1 | * | 4/2003 | Fitzgerald | G08B 3/10 340/573.1 |
| 2003/0078071 A1 | * | 4/2003 | Uchiyama | H04M 1/006 455/557 |
| 2003/0122676 A1 | * | 7/2003 | Cuijpers | H03G 3/32 340/573.1 |
| 2004/0003073 A1 | * | 1/2004 | Krzyzanowski | H04L 12/2803 709/223 |

(Continued)

FOREIGN PATENT DOCUMENTS

CN 104571480 A * 4/2015
HK DE 102006058540 A1 * 8/2007 .............. G08B 3/10

*Primary Examiner* — Jay Au
*Assistant Examiner* — Joseph Suh
(74) *Attorney, Agent, or Firm* — Henry J. Cittone; Cittone & Chinta LLP (57) ABSTRACT

A monitoring unit system is provided having a parent unit whose speaker is muted when a wrist unit is activated, where the wrist unit vibrates, the parent unit or wrist unit lights up, the wrist unit continues to alert until a mute button is pressed, or if a predetermined time elapses, alerts the parent unit, and having a low battery trigger, a fail-safe wrist unit and parent unit out of range trigger, a page button for the wrist unit and parent unit, a mute feature on the baby unit, and a cry duration or volume threshold trigger.

17 Claims, 6 Drawing Sheets

(56) References Cited

U.S. PATENT DOCUMENTS

| | | | | |
|---|---|---|---|---|
| 2004/0197082 A1* | 10/2004 | Yim | ............... | H04N 5/782 386/259 |
| 2005/0108751 A1* | 5/2005 | Dacosta | ............... | G06F 3/0482 725/39 |
| 2005/0123144 A1* | 6/2005 | Wallace | ............... | H04R 3/007 381/56 |
| 2005/0201541 A1* | 9/2005 | Berezowski | ............ | G08B 3/10 379/170 |
| 2005/0280704 A1* | 12/2005 | Clare | ............... | G08B 13/1672 348/143 |
| 2006/0068818 A1* | 3/2006 | Leitersdorf | ............ | H04H 20/18 455/466 |
| 2006/0116073 A1* | 6/2006 | Richenstein | ............ | H04H 20/62 455/3.06 |
| 2006/0205432 A1* | 9/2006 | Hawkins | ............ | H04M 1/27455 455/552.1 |
| 2007/0055876 A1* | 3/2007 | Choi | ............... | G06F 13/4081 713/170 |
| 2007/0058039 A1* | 3/2007 | Clark | ............... | A63H 33/006 348/143 |
| 2007/0241911 A1* | 10/2007 | Swan | ............... | G08B 13/19621 340/573.1 |
| 2007/0284401 A1* | 12/2007 | Hilliard | ............... | G04F 1/005 222/638 |
| 2008/0018459 A1* | 1/2008 | Derrick | ............... | G07C 1/20 340/539.13 |
| 2008/0075295 A1* | 3/2008 | Mayman | ............... | G06F 1/1632 381/79 |
| 2009/0018841 A1* | 1/2009 | Leeds | ............... | A63H 3/28 704/272 |
| 2009/0046863 A1* | 2/2009 | Gude | ............... | H04R 1/403 381/1 |
| 2009/0191850 A1* | 7/2009 | Cardwell, III | ............ | G08B 25/016 455/412.2 |
| 2009/0316000 A1* | 12/2009 | Weinblatt | ............ | H04N 17/004 348/180 |
| 2010/0050064 A1* | 2/2010 | Liu | ............... | G06F 17/2765 715/202 |
| 2010/0079106 A1* | 4/2010 | Graham | ............... | H02J 7/0044 320/115 |
| 2011/0050419 A1* | 3/2011 | Ng | ............... | E05B 39/00 340/542 |
| 2011/0230115 A1* | 9/2011 | Wang | ............... | A63H 33/006 446/227 |
| 2012/0057517 A1* | 3/2012 | Kambhatla | ............ | H04W 28/02 370/315 |
| 2012/0115544 A1* | 5/2012 | Seguie | ............... | G08B 21/0208 455/557 |
| 2014/0035516 A1* | 2/2014 | Fratti | ............... | H02J 7/0013 320/108 |
| 2014/0228649 A1* | 8/2014 | Rayner | ............... | A61B 5/1118 600/301 |
| 2015/0163412 A1* | 6/2015 | Holley | ............... | G05B 15/02 348/143 |
| 2015/0279187 A1* | 10/2015 | Kranz | ............... | G08B 21/0415 340/539.12 |
| 2015/0280892 A1* | 10/2015 | Verbin | ............... | H04L 5/0007 370/294 |
| 2016/0005292 A1* | 1/2016 | Carroll | ............... | G08B 21/088 340/539.13 |

* cited by examiner

NON-DISRUPTIVE MONITOR SYSTEM

BACKGROUND

Caregivers often use monitor systems to observe and/or hear their babies while they sleep in another room. These monitors are composed of a parent unit which receives sound and/or video from a monitoring unit (often referred to as a baby, kid or child unit) capable of recording and transmitting sound and/or video. Transmission is typically wireless.

Such monitors typically transmit all sounds and video from the monitored room on a continuous basis for playing by the parent unit. More advanced monitors will key a microphone to transmit only when sounds above a certain decibel are received. This avoids broadcasting sounds from normal sleep activity and movement. Since the parental unit simply plays the sound and/or video via a speaker, in two parent households, both parents are woken whenever an event triggers the transmission of sound or when a loud-enough sound is broadcast by the parent unit.

SUMMARY OF THE INVENTION

In aspects of the present invention a monitor system is provided which features one or more of: (1) a parent unit speaker which is muted when the mobile or wrist unit is activated, (2) a wrist unit which vibrates, (3) a parent unit and/or wrist unit which lights up or makes or plays broadcast sound, (4) a wrist unit which continues to alert until a mute button is pressed, and which may eventually alert on the parent unit if no response occurs from the wrist unit, (5) a low battery trigger, (6) a fail-safe parent unit out of range trigger, (7) a page button for the wrist unit or parent unit, (8) a mute feature on a monitoring unit, and/or (9) a noise duration threshold to trigger a wrist unit or parent unit.

In one aspect the system comprises a parent unit, a monitoring unit (also referred to as a baby unit or child unit) which may be located in proximity to the person, animal, object, location or room being monitored and a wrist unit.

BRIEF DESCRIPTION OF THE DRAWINGS

The invention will hereinafter be described in conjunction with the figures provided herein to further illustrate various non-limiting embodiments of the invention, wherein like designations denote like elements, and in which.

DETAILED DESCRIPTION OF THE INVENTION

Broadly described, the present invention comprises a primary receiving unit, a monitoring unit, one or more charging docks, and one or more secondary receiving units which are configured to be in communication with one another such that the primary receiving unit does not disturb an off-duty guardian unless the on-duty guardian fails to respond to a communication (also referred to herein as an alert) from the monitoring unit. The present invention is now described with reference to particular embodiments, for example a child or baby monitor system, but it is understood that many embodiments and variations fall within the scope of the present invention and disclosure and that the method of use of the monitoring system is not limited to the monitoring of children or babies and can include any circumstance where a room, individual or animal requires monitoring. In such examples the primary receiving unit may be referred to as the "parent unit", the monitoring unit as the "child" or "baby unit", and one or more secondary receiving units as "wrist unit(s)".

Figure 1:
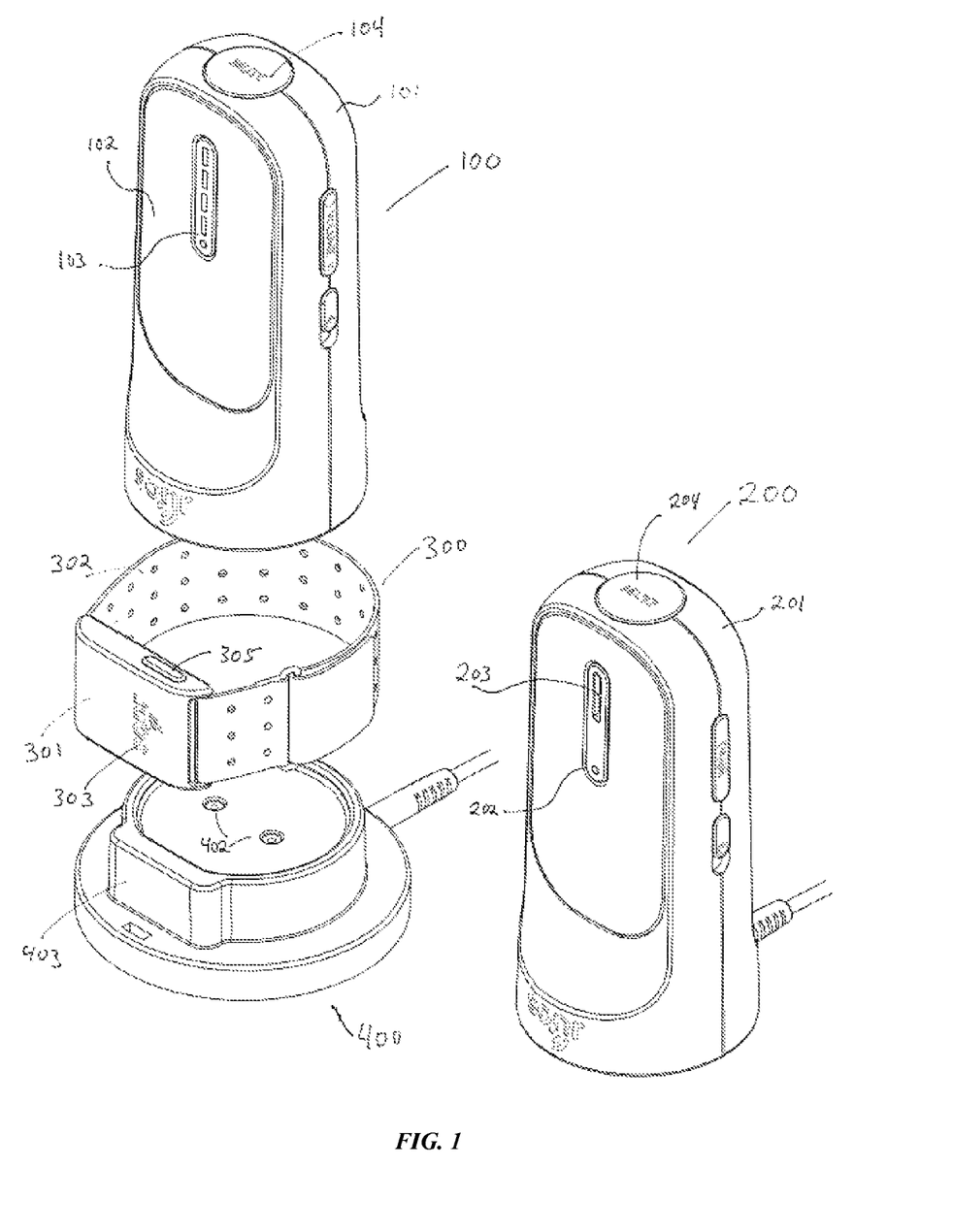
FIG. 1 is a perspective view of the parent, child, wrist unit and a charging dock of an embodiment of the present invention.
Figure 2:
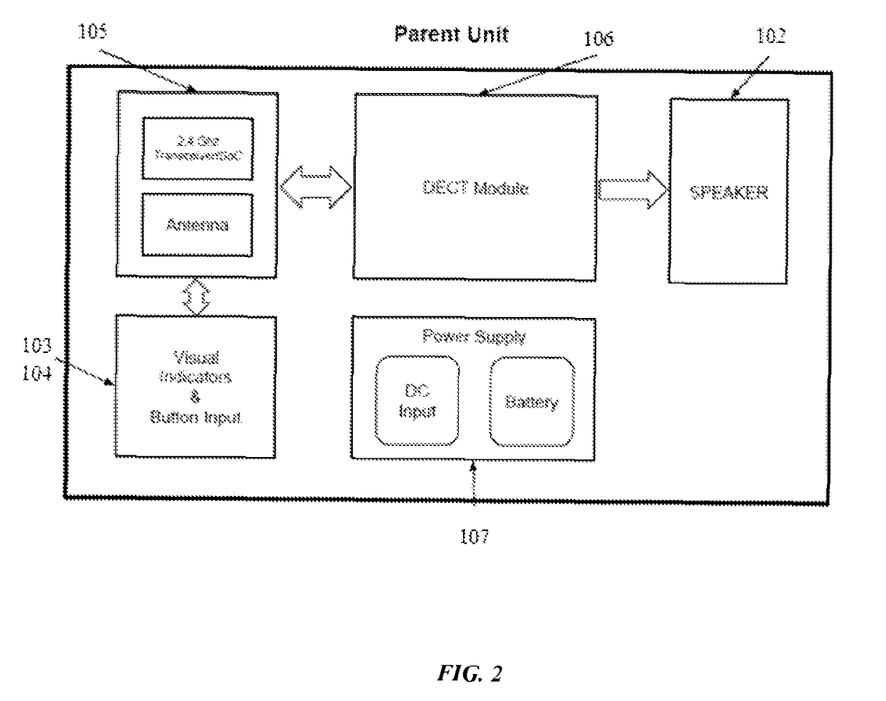
FIG. 2 is a block diagram of the electronics of a parent unit of an embodiment of the present invention.

More particularly, referring now to FIGS. 1 and 2, the parent unit 100 has a housing 101 which houses an audio speaker 102, visual indicators 103 and button input 104, a 2.4 Ghz transceiver/SoC (system on a chip) and antenna 105, and a DECT (digital enhanced cordless telecommunications) module 106, and connectivity to a power supply.

The audio speaker 102 serves to broadcast sound data that has been sent from the child unit to the parent unit. Visual indicators 103 serve to indicate device on/off status, mute status, audio decibel range, or the paging of other devices. Visual indicators 103 may be, for example, light emitting diodes (LEDs). Button input 104 serves to turn the device on/off, control volume, mute or page other devices. It is understood that the button input 104 may be one button configured to control the aforementioned functions via length of depression, repetition of depressions, or other codes, or may be multiple buttons with each serving one or more of the aforementioned functions.

The 2.4 Ghz transceiver/SoC and antenna 105 serves to carry out logic as defined by device firmware and communicates with the wrist unit described below via a built in transceiver which utilizes the antenna to transmit and receive data. The DECT module 106 enables the transmission of audio and other data between the baby unit and the parent unit and has a built in antenna. A power supply 107 provides power circuitry to facilitate the operating requirements of the other components of parent unit 100. The parent unit may be powered by one or more of direct current (DC), alternating current (AC) or battery power, though preferably it is powered by an AC/DC adaptor. Optionally, the parent unit may have a video display and related circuitry to receive video signals from a camera on the monitoring unit and to optionally display temperature data received from the monitoring unit. It is generally understood that the electronics within the parent unit 100 may be configured in multiple manners to provide the capabilities and functions described herein.

Figure 3:
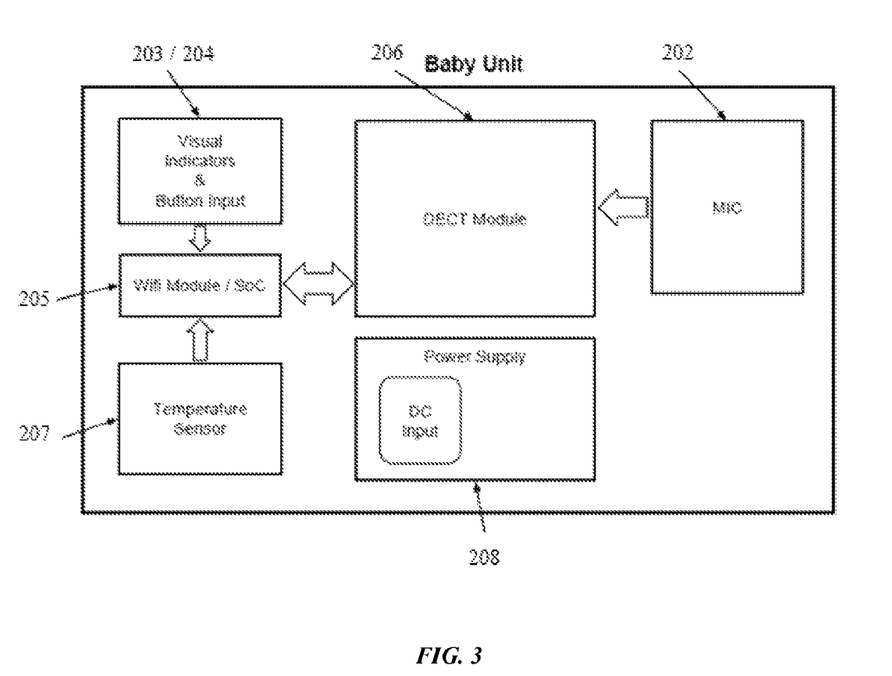
FIG. 3 is a block diagram of the electronics of a monitoring unit of an embodiment of the present invention.

Referring now to FIGS. 1 and 3, the monitoring unit 200 has a housing 201 which houses a microphone 202, a visual indicator 203, a button input 204, a Wifi module/SoC 205, a DECT module 206, a temperature sensor 207, and a power supply 208.

The microphone 202 serves to pick up sound and covert it to electrical signals. Visual indicator 203 has LED's which indicate whether the device is on/off, muted, or paging other devices. Button input 204 serves to turn the device on/off, mute, or page. It is understood that the button input 204 may be one button configured to control the aforementioned functions via length of depression, repetition of depressions, or other codes, or may be multiple buttons with each serving one or more of the aforementioned functions. Wi-Fi (wireless local area network) module/SoC 205 serves to handle logic as defined by firmware and has a built in Wi-Fi transceiver and antenna. DECT module 206 serves to enable the transmission of audio and other data between the monitoring unit 200 and the parent unit 100 and has a built in antenna. Temperature sensor 207 serves to detect the temperature of the monitoring unit location and communicates temperature data to a display and optionally for transmission via Wi-Fi and the DECT module. The power supply 208 provides power circuitry to facilitate the operating requirements of the other components of monitoring unit 200. Optionally monitoring unit 200 also includes a camera configured to provide video data to the Wi-Fi module 205 and/or DECT module 206 for transmission to the parent unit 100 or to a smartphone configured with application software to receive data from the monitoring unit 200.

Figure 4:
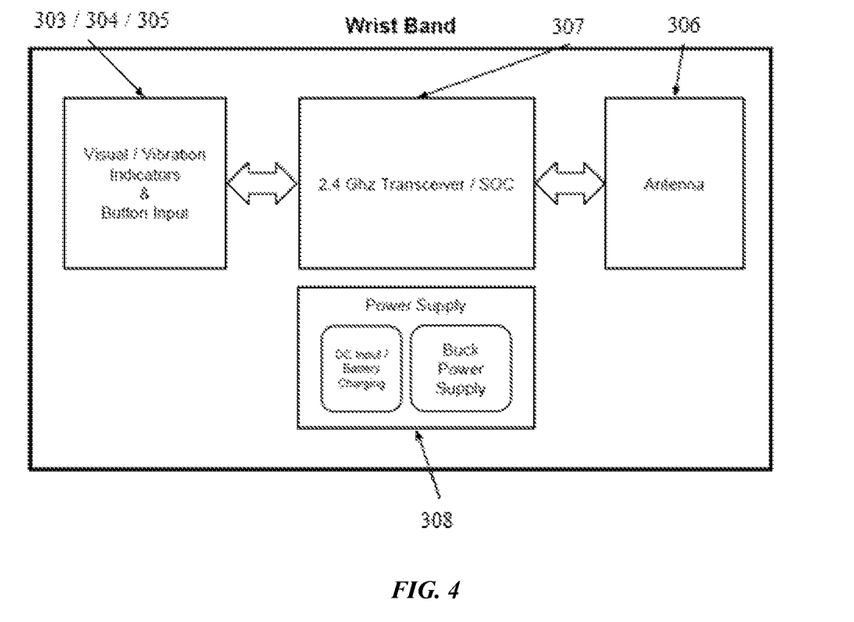
FIG. 4 is a block diagram of the electronics of a mobile or wrist unit of an embodiment of the present invention.

Referring now to FIGS. 1 and 4, the mobile or wrist unit 300 has a housing 301 attached to a band 302 capable of being worn on a human wrist. Housing 301 houses visual indicators 303, vibration indicator 304, button input 305, an antenna 306, a 2.4 Ghz transceiver SoC 307 and a power supply 308.

The visual indicators 303, vibration indicator 304, and button input 305 serve to provide a user interface for controlling and receiving information via the wrist unit. The visual indicators 303 may be LEDs and serve to provide information concerning on/off status, mute status, audio decibel range, or the paging of other devices. The vibration indicator 304 may be a vibrating motor. The button input 305 allows a user to silence or activate an alert. The antenna 306 is preferably suitable for 2.4 Ghz radio reception. The 2.4 Ghz transceiver SoC 307 serves to handle logic and communication for the wrist unit 300.

Referring now to FIG. 1, the charging dock 400 includes an AC to DC adapter 401 and one or more DC outputs 402 in a housing 403. For example, in a charging dock with multiple DC outputs 402, the DC outputs 402 can charge parent units 100 and wrist units 300. The AC/DC adapter may, for example provide 5 Volt DC power to aforementioned units. Alternatively, in other embodiments of the present invention, one or more of the wrist unit or parent units or child units may be charged by induction coils, and are so configured, and the charging dock 400 is configured to include an induction charging mechanism.

In an alternative embodiment one or more of the parent unit and monitoring unit are wifi capable, and can communicate to application software on a mobile device such as a smartphone to provide all notification functions. Application software on said mobile device also provides all communication functions to the parent unit as described herein.

In yet a further embodiment, the system of the present invention may be deployed entirely or in part by application software on network capable devices, preferably wireless capable, equipped with at least microphones and speakers, and preferably display screens, more preferably touch screens. The network capable devices serve as one or more of the parent unit, monitoring unit and mobile unit and utilize an existing WiFi, cellular or other wireless network. Examples of network capable devices include smartphones, tablet computing devices, and cellular phones, all capable of running application software. Graphical user interfaces on one or more of the parent unit, monitoring unit and mobile unit provide the aforementioned visual indicator functions of visual indicators 103, 203 and 303. Button inputs 104, 204 and 305 are provided by touch-screen functionality or manual input buttons on the network capable devices and the vibration is provided by a built in vibrate function such as the vibrate ring of the network capable devices. Alternatively the aforementioned network capable devices may function across a wired network, though preferably at least the mobile unit functions across a wireless network.

Figure 5A:
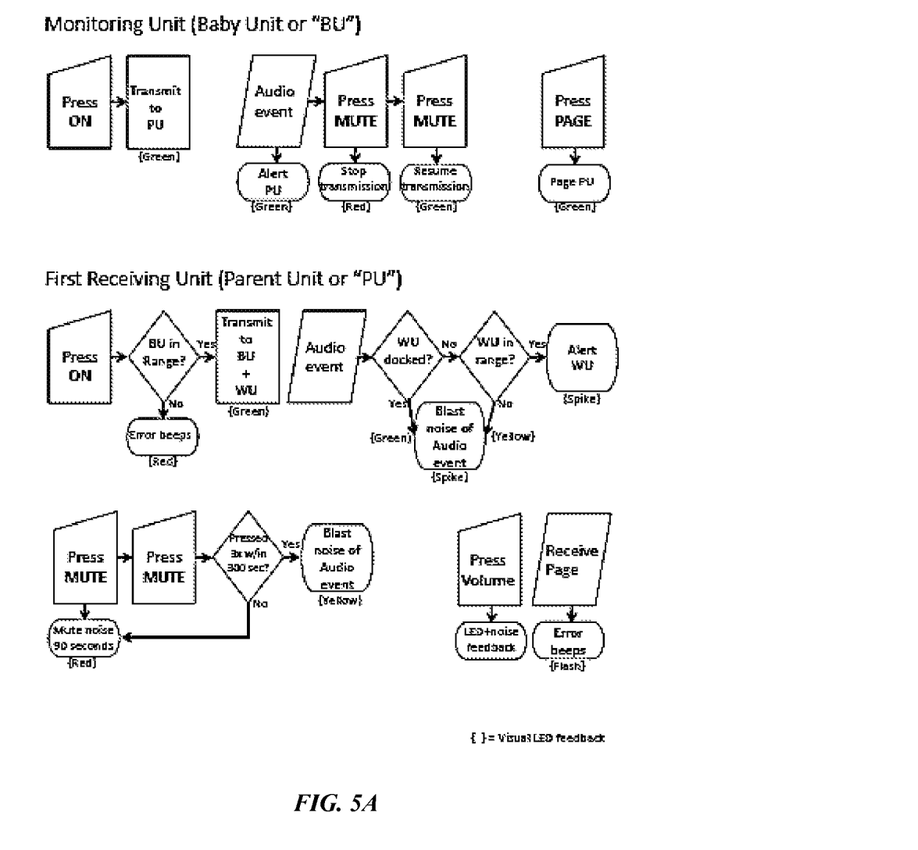
FIGS. 5A and 5B are flowcharts of a method of an embodiment of the present invention.
Figure 5B:
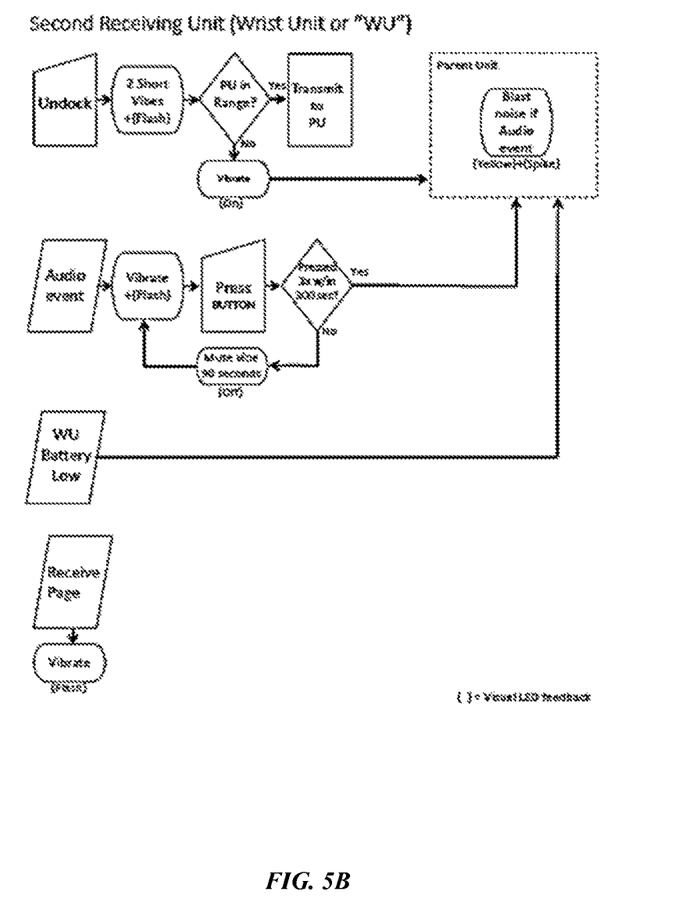

When in use, the system functions to allow guardians, which may be parents, to be on or off duty in responding to the monitored room or person's needs, for example a child's. This is accomplished by use of the wrist band 300 worn by the on duty guardian and the primary receiving unit settings. Referring now to FIGS. 5A and 5B, logical functions are carried out via firmware or software code, an exemplary embodiment of which follows and in which the guardian is a parent, the primary receiving unit is a parent unit, the monitoring unit is a child unit and the secondary receiving unit is a wrist unit:

The child unit 200 is turned on, with the "on" LED showing green. When powered on, the child unit 200 transmits audio events to the parent unit 100. Audio events may be actual crying or other noises of a predetermined decibel level or higher. The predetermined decibel level may be preset in the system or selected by the user upon set up. When an audio event is detected by the child unit 200 it transmits a notification to the parent unit 100. As described below, the parent unit decides whether to issue an alert via the speaker on the parent unit or send a notification to the wrist unit based upon whether the wrist unit is docked or undocked and whether the on duty parent responds to their alert in time.

Upon responding, the on duty parent may mute the parent unit 100 to prevent additional notifications by pressing a "mute" button on the child unit 200. Transmissions to the parent unit 100 may be resumed by pressing the mute button once again, for example once the situation with the child is resolved. The on duty parent may also notify the off duty parent by pressing the page button on the child unit, which will transmit the page notification to the parent unit 100. A page notification may be actual audio of the cry event or a chime or alarm sound of any kind any of which is broadcast loudly enough to wake an off duty parent. As discussed below, when used with a functioning wrist unit 300, the parent unit 100 will not disturb the off duty parent.

Referring again to FIGS. 1 and 5, when the parent unit 100 is turned on it determines whether there is a child unit 200 in range by checking for transmission from the child unit 200. If no child unit 200 is detected the parent unit 100 will initiate an alarm condition. The alarm condition may for example be provided via the audio speaker 102 and one or more LEDs 103 which may glow or flash red. If a child unit 200 is detected in range, the parent unit 100 will be in a functional state, and the LED 103 may glow green for example to indicate such, and the speaker 102 will be on. Alternatively, a parent unit 100 LED will glow green when a wrist unit 300 is connected to the parent unit and charging or disconnected from the parent unit and in range. The parent unit 100's LED may instead glow yellow for example when a wrist unit 300 is detached and not in range.

Turning now to the situation where the wrist unit 300 is not detected by the parent unit 100, upon detecting an alert event from the child unit 200, the parent unit speaker is set to "on" and the parent unit 100 will broadcast its alert via sound from the audio speaker 102 and optionally LED indicators 103 may flash or spike to indicate noise level. When the parent unit speaker 102 is in an "on" status the parent unit 100 mute function may be activated by the user. If the mute function is activated the speaker is set to an "off" status for, for example, 90 seconds. As a failsafe, if mute is pressed repeatedly, for example three times within 270 seconds, then the parent unit speaker is set to an "on" status regardless of further muting requests allowing alerts to be broadcast loudly enough to wake any persons near the parent unit 100, typically any sleeping parents in this example. If the page function is activated, the wrist unit 300 will be alerted.

When a wrist unit 300 is undocked from the charging dock 400, it may vibrate twice and optionally an LED 303 may flash indicating it is now in an active state. If the wrist unit 300 can receive transmission from the parent unit 100 upon undocking, it will cease vibrating and flashing its LED, indicating it is now active.

When a wrist unit 300 is not charging and is detected in range, the parent unit 100's speaker 102 is set to an "off" status and upon an audio event the parent unit 100 will transmit an event notification to the wrist unit 300. Optionally, LED level indicators 103 will indicate the noise level of the audio event.

Upon receiving notification of an audio event from the parent unit 100 the wrist unit 300 will alert via vibration 304 and optionally LED 303 activation. Upon an alert the on duty parent using the wrist unit may mute using the mute function 305. As a failsafe, if mute is signaled repeatedly, for example three times within 270 seconds, then the parent unit speaker 102 is set to an "on" status regardless of further muting requests allowing alerts to be broadcast loudly enough to wake any persons near the parent unit, typically any sleeping parents in this example.

If for some reason the wrist unit 300 cannot receive transmissions from the parent unit 100 (for example the wrist unit 300 is out of range, or the parent unit is offline), then it will initiate an alarm condition and for example may vibrate once for a longer duration and optionally its LED may flash. Simultaneously, if for some reason the parent unit 100 cannot receive transmissions from the wrist unit 300 (for example the wrist unit 300 is out of range or low on battery), the parent unit 100's LEDs 103 may glow yellow and the parent unit speaker 102 is set to an "on" status allowing alerts to be broadcast loudly enough to wake any persons near the parent unit.

Each of the parent unit 100, child unit 200 and wrist unit 300 may have a low battery warning condition and suitable battery monitoring circuitry which activates a low battery alert warning, which warning may be sound, LED color, flashing or other predetermined low battery alert.

It is understood that the parent unit 100 and child unit 200 is sufficient to serve as a monitor system without the wrist unit 300. It is further understood that the alert status condition may be predetermined by one or more of volume of sound detected, duration of sound detected, or type of sound detected—for example background noises may be filtered or ignored while child cries or other sounds of human voice selectively registered by the child unit 200. Lastly it is understood that while in this example the parent unit 100 is transmitting data to the wrist unit 300, it is equally possible for the foregoing tasks described above to be partitioned between any of the three or more units within the system and for such units to communicate via the Internet, cellular networks, wireless networks and the like.

The invention claimed is:

1. A system comprising:
   (a) a monitoring unit having a microphone and a transmitter in communication with a first receiving unit, wherein the monitoring unit is capable of detecting and recording an audible event and transmitting the audible event to a first receiving unit;
   (b) the first receiving unit having a receiver, a transmitter and a speaker, wherein the first receiving unit is capable of detecting the presence of a predetermined condition on the monitoring unit, the first receiving unit or a second receiving unit; and
   (c) the second receiving unit having a receiver, a transmitter in communication with the first receiving unit and an alert function,
   wherein the first receiving unit is capable of broadcasting the audible event unless the second receiving unit is detected by the first receiving unit and the predetermined condition has not been detected on the monitoring unit, the first receiving unit or the second receiving unit,
   wherein when active, the second receiving unit causes deactivation of the speaker of the first receiving unit, and wherein the monitoring unit has a page button which activates the speaker of the first receiving unit and the alert function of the second receiving unit.

2. The first receiving unit of claim 1 further comprising a page function wherein the page function activates an alert on the second receiving unit.

3. The first receiving unit of claim 1 further comprising a page function wherein the page function activates an alert on the second receiving unit wherein the alert is vibration.

4. The first receiving unit of claim 1 further comprising a mute function wherein the mute function mutes the speaker of the first receiving unit.

5. The system of claim 1 further comprising a fail-safe sub-system and a response button, wherein the fail-safe system will place the second receiving unit in an off state if no response is sent from the second receiving unit to the first receiving unit.

6. The system of claim 1 wherein the second receiving unit transmits a signal to the first receiving unit on a periodic basis wherein, if the first receiving unit does not receive the signal within a predetermined time, its speaker enters an active state.

7. The system of claim 1 wherein the first receiving unit has a video display and the monitoring unit has a camera, wherein the monitoring unit transmits video to the first receiving unit.

8. The system of claim 1 wherein the monitoring unit has a mute button which either (a) terminates transmissions from the monitoring unit or (b) continues to transmit but ensures that any transmissions are not broadcast by the speaker of the first receiving unit.

9. The system of claim 1 wherein the first receiving unit has a mute button which either (a) terminates transmissions from the monitoring unit for a predetermined period of time or (b) elects not to broadcast any transmissions via its speaker.

10. The system of claim 1 wherein the first receiving unit has a page button which activates the alert function on the second receiving unit.

11. The system of claim 1 wherein the second receiving unit has a mute button which terminates transmissions from the first receiving unit for a predetermined period of time or (b) elects not to trigger its alert function.

12. The system of claim 1 wherein the second receiving unit has a page button which activates the speaker of the first receiving unit.

13. The system of claim 1 wherein the first receiving unit is in communication with the monitoring unit and the second receiving unit via the Internet or a wireless network.

14. The system of claim 1 wherein the second receiving unit is charged by a docking station.

15. The system of claim 1 wherein the predetermined condition is a repeated use of a mute function on the monitoring unit, the first receiving unit or the second receiving unit.

16. The system of claim 1 wherein if the first receiving unit does not broadcast the audible event, an alert occurs on the second receiving unit.

17. The system of claim 1 wherein the alert occurring on the second receiving unit is one or more of a vibration, sound or LED flash.

* * * * *